US010617880B2

(12) United States Patent
Zellmer et al.

(10) Patent No.: US 10,617,880 B2
(45) Date of Patent: Apr. 14, 2020

(54) SYSTEM AND METHOD FOR AN ELECTRICAL IMPLANT DEVICE WITH INCREASED PATIENT COMPLIANCE

(71) Applicant: Intelligent Implants Limited, Ballintemple (IE)

(72) Inventors: Erik Zellmer, St. Louis, MO (US); John Zellmer, Hovås (SE); Rory Murphy, San Francisco, CA (US)

(73) Assignee: Intelligent Implants Limited, Cork (IE)

( * ) Notice: Subject to any disclaimer, the term of this patent is extended or adjusted under 35 U.S.C. 154(b) by 153 days.

(21) Appl. No.: 15/373,237

(22) Filed: Dec. 8, 2016

(65) Prior Publication Data

US 2017/0157407 A1 Jun. 8, 2017

Related U.S. Application Data

(60) Provisional application No. 62/264,840, filed on Dec. 8, 2015, provisional application No. 62/278,979, filed on Jan. 14, 2016.

(51) Int. Cl.
*A61N 1/37* (2006.01)
*A61N 1/378* (2006.01)
(Continued)

(52) U.S. Cl.
CPC .............. *A61N 1/3787* (2013.01); *A61F 2/44* (2013.01); *A61F 2/4455* (2013.01); *A61N 1/326* (2013.01);
(Continued)

(58) Field of Classification Search
CPC .. A61N 1/3787; A61N 1/37282; A61N 1/326; A61N 1/3605; A61F 2/4465;
(Continued)

(56) References Cited

U.S. PATENT DOCUMENTS 1,029,831 A 6/1912 Teed
4,313,438 A 2/1982 Greatbatch
(Continued)

FOREIGN PATENT DOCUMENTS

WO 2013188380 A1 12/2013
WO 2014089299 A3 10/2014

OTHER PUBLICATIONS

Laughner JI, et al. (2013) A Fully Implantable Pacemaker for the Mouse: From Battery to Wireless Power. PLOS One 8(10): e76291. https://doi.org/10.1371/journal.pone.0076291, Oct. 23, 2013.
(Continued)

*Primary Examiner* — Rex R Holmes
(74) *Attorney, Agent, or Firm* — Alpine Patents LLC; Brian Van Osdol

(57) ABSTRACT

A system and method for powering a medical device that includes a fixture configured for periodic patient proximity; external electrical coupling device integrated into the fixture wherein the external electrical coupling device comprises at least one external energy coupler and is configured to detect presence of an electrical medical device implant in a transmission zone of the external electrical coupling device; an electrical medical device implant, wherein the electrical medical device implant comprises at least one implant energy coupler; and wherein the external electrical coupling device is configured to couple to the implantable medical device through a wireless energy transmission between the external energy coupler and the implant energy coupler when presence of the implantable medical device is within a transmission zone.

21 Claims, 17 Drawing Sheets

(51) Int. Cl.

| | |
|---|---|
| ***A61N 1/32*** | (2006.01) |
| ***A61N 1/36*** | (2006.01) |
| ***A61N 1/372*** | (2006.01) |
| ***A61F 2/44*** | (2006.01) |
| *A61F 2/48* | (2006.01) |
| *H02J 50/40* | (2016.01) |
| *A61F 2/30* | (2006.01) |
| *H02J 50/10* | (2016.01) |
| *A61F 2/46* | (2006.01) |
| *H02J 50/80* | (2016.01) |

(52) U.S. Cl.

CPC ....... *A61N 1/3605* (2013.01); *A61N 1/37282* (2013.01); *A61F 2002/3067* (2013.01); *A61F 2002/4475* (2013.01); *A61F 2002/469* (2013.01); *A61F 2002/482* (2013.01); *H02J 50/10* (2016.02); *H02J 50/40* (2016.02); *H02J 50/80* (2016.02)

(58) Field of Classification Search

CPC .............. A61F 2/4455; A61F 2002/469; A61F 2002/4475; A61F 2002/3067; A61F 2002/30668; A61F 2002/30187; A61F 2002/482; H02J 50/10; H02J 50/40; H02J 50/80

See application file for complete search history.

(56) References Cited

U.S. PATENT DOCUMENTS

| | | | | |
|---|---|---|---|---|
| 4,690,166 | A | 9/1987 | Howeth | |
| 5,565,005 | A | 10/1996 | Erickson et al. | |
| 5,974,342 | A | 10/1999 | Petrofsky | |
| 5,989,289 | A | 11/1999 | Coates et al. | |
| 6,120,502 | A | 9/2000 | Michelson | |
| 6,292,699 | B1 | 9/2001 | Simon et al. | |
| 6,400,990 | B1 | 6/2002 | Silvian | |
| 6,582,467 | B1 | 6/2003 | Teitelbaum et al. | |
| 6,605,089 | B1 | 8/2003 | Michelson | |
| 7,104,986 | B2 | 9/2006 | Hovda et al. | |
| 7,309,338 | B2 | 12/2007 | Cragg | |
| 7,324,852 | B2 | 1/2008 | Barolat et al. | |
| 7,359,755 | B2 | 4/2008 | Jones et al. | |
| 7,455,672 | B2 | 11/2008 | Michelson | |
| 7,578,819 | B2 | 8/2009 | Bleich et al. | |
| 7,935,116 | B2 | 5/2011 | Michelson | |
| 8,014,873 | B2 | 9/2011 | Jones et al. | |
| 8,078,282 | B2 | 12/2011 | Nycz | |
| 8,078,283 | B2 | 12/2011 | Cowan et al. | |
| 8,206,387 | B2 | 6/2012 | Michelson | |
| 8,463,401 | B2 | 6/2013 | Jones et al. | |
| 8,740,879 | B2 | 6/2014 | Martinson et al. | |
| 8,771,360 | B2 | 7/2014 | Jimenez et al. | |
| 8,903,502 | B2 * | 12/2014 | Perryman ............ | A61N 1/0558<br>607/72 |
| 2003/0078634 | A1 * | 4/2003 | Schulman ................ | A61N 1/08<br>607/61 |
| 2005/0033393 | A1 | 2/2005 | Daglow | |
| 2007/0250045 | A1 | 10/2007 | Trieu | |
| 2008/0294211 | A1 | 11/2008 | Moffitt | |
| 2008/0300660 | A1 * | 12/2008 | John .................... | A61N 1/3785<br>607/61 |
| 2009/0062886 | A1 | 3/2009 | O'Handley et al. | |
| 2011/0092948 | A1 | 4/2011 | Shachar et al. | |
| 2013/0150970 | A1 | 6/2013 | Thaiyananthan | |
| 2013/0296940 | A1 | 11/2013 | Northcutt et al. | |
| 2014/0114382 | A1 | 4/2014 | Kim | |
| 2014/0275847 | A1 | 9/2014 | Perryman et al. | |
| 2014/0277260 | A1 | 9/2014 | Khalil et al. | |
| 2014/0371823 | A1 | 12/2014 | Mashiach et al. | |
| 2015/0018728 | A1 * | 1/2015 | Gross ..................... | A61N 5/022<br>601/46 |
| 2015/0134061 | A1 | 5/2015 | Friis et al. | |
| 2017/0157407 | A1 | 6/2017 | Zellmer et al. | |

OTHER PUBLICATIONS

WIPO European Searching Authority, "PCT2016000482 WO Search and Opinion", dated Jul. 7, 2016.

* cited by examiner

FIGURE 6A
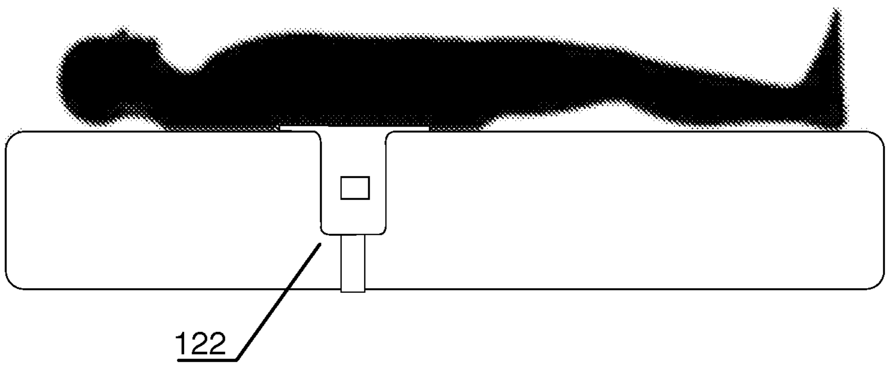
FIGURE 6B
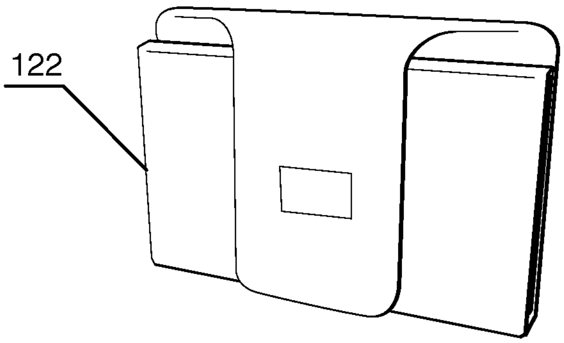
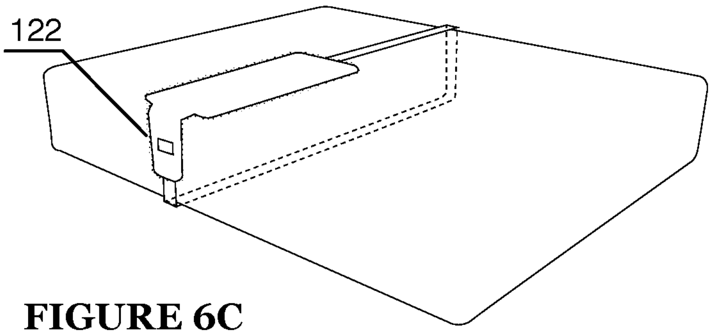
FIGURE 6C

130

SYSTEM AND METHOD FOR AN ELECTRICAL IMPLANT DEVICE WITH INCREASED PATIENT COMPLIANCE

CROSS-REFERENCE TO RELATED APPLICATIONS

This Application claims the benefit of U.S. Provisional Application No. 62/264,840, filed on 8 Dec. 2015 and U.S. Provisional Application No. 62/278,979, filed on 14 Jan. 2016, both of which are incorporated in their entireties by this reference.

TECHNICAL FIELD

This invention relates generally to the field of surgical implants, and more specifically to a new and useful system and method for an electrical implant device used to increase patient compliance, thereby increasing overall treatment efficiency.

BACKGROUND

Patient compliance is an important factor to recovery after a surgery. New devices can provide numerous healing benefits but only when the patient follows through with extra tasks. Thus, there is a need in the surgical implant field to create a new and useful system and method for an electrical implant device with increased patient compliance. This invention provides such a new and useful system and method.

BRIEF DESCRIPTION OF THE FIGURES

FIGS. 6A-6C are schematic representations of a bedding system;

DESCRIPTION OF THE EMBODIMENTS

Figure 1:
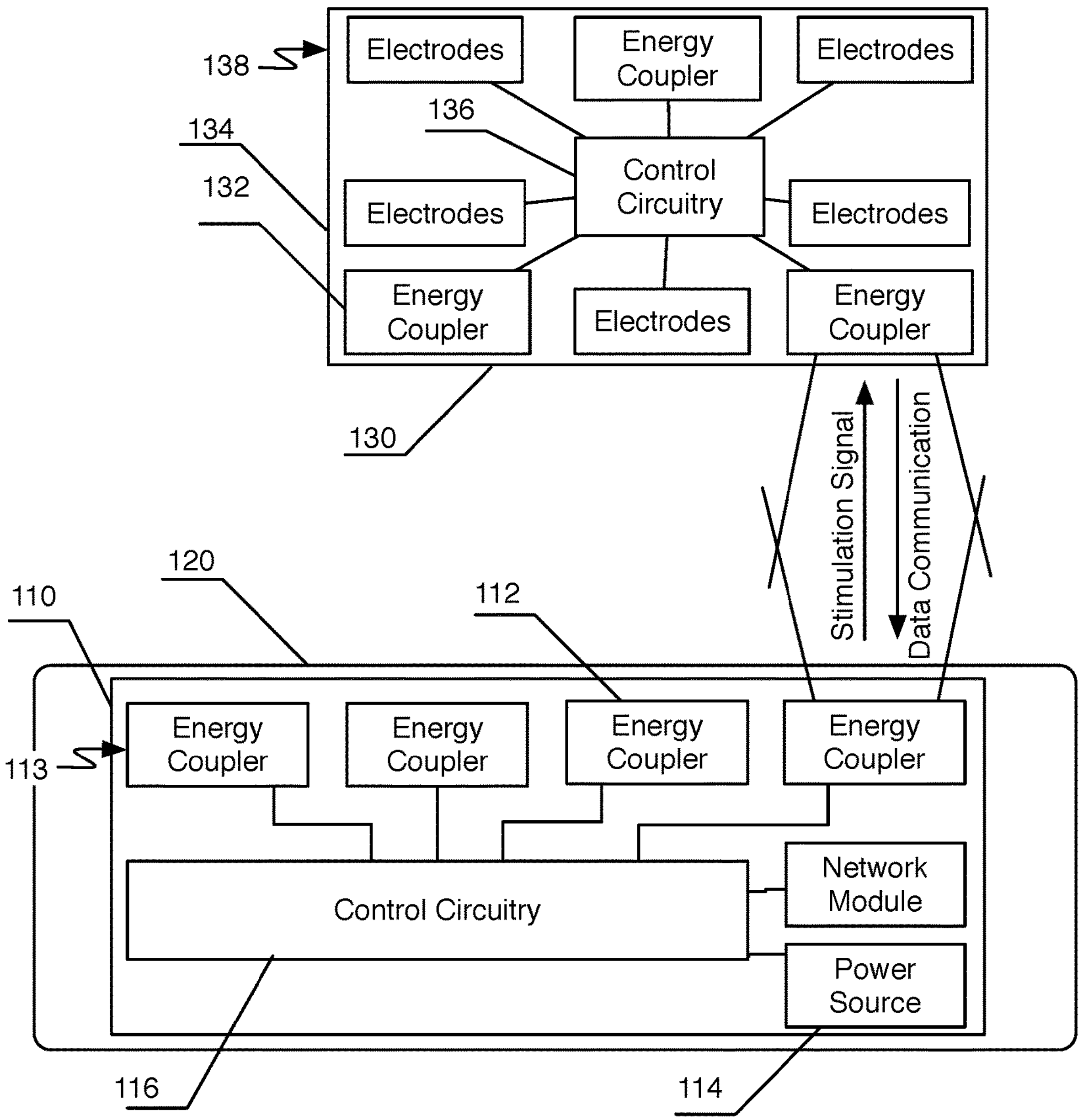
FIG. 1 is a schematic representation of a system of a preferred embodiment.

The following description of the embodiments of the invention is not intended to limit the invention to these embodiments but rather to enable a person skilled in the art to make and use this invention.

1. Overview

A system and method for an electrical implant device with increased patient compliance functions to provide wireless electrical power and/or communication with a subcutaneous implant through commonly encountered fixtures. Through integrating an external electrical coupling device into commonly used fixtures such as a bed, a seat, or a support brace, a patient with a surgical implant can receive stimulation during normal, routine activities, which functions to increase patient compliance of using external charging and/or stimulation of the implant. More specifically, the system and method can enable a patient to have a surgically installed implant to be charged or electrically stimulated by a bedding system, seating system, a wearable fixture like a corset, or other suitable fixture. From the patient perspective, electrical coupling of the external electrical coupling device is performed transparently with no extra effort from the patient perspective. The patient can go about their daily routine and the electrical implant can receive sufficient energy coupling when the patient sleeps or sits in a chair. The electrical coupling may be used for powering or charging the electrical components of the implant, driving stimulation or activation of the implant, and/or communicating with the implant. The fixtures used in facilitating electrical stimulation can be characterized as providing electrical coupling during non-restrictive positioning. For example, the bedding or seating system can provide stimulation over a wide range of patient positioning relative to the implant stimulation device.

As described herein, the system and method are preferably applied to implants for subcutaneous electrical stimulation and more specifically applied to electrically stimulating spinal fusion implants. In one implementation, the system and method can be used in combination with a spinal fusion implant system and methods described in U.S. patent application Ser. No. 15/075,152, titled "SYSTEM AND METHOD FOR DYNAMICALLY STIMULATING BONE GROWTH", filed 19 Mar. 2016, which is hereby incorporated in its entirety by this reference. The system and method may alternatively be applied to other forms of orthopedic implants that benefit from osteoinduction and/or osteolysis. The system and method may additionally be applied more broadly to other forms of medical device implants, in particular, ones that may benefit from regular but non-critical stimulation such as implants used for stimulation of the peripheral and/or central nervous system. The system and method may alternatively be applied to other electrical-based implants or internal medical devices that can be configured for wireless charging and/or wireless communication.

As a first potential benefit, a system and method of a preferred embodiment may be used to increase patient compliance. Electrical implants may benefit from regular and routine use. In the case of spinal fusion implants or other electrical stimulation implants, external electrical coupling is preferred to enable regular electrical stimulation by the implant. A patient can be alleviated of needing to wear a special device for long durations, because electrical stimulation may be performed when resting or sleeping in bed, when sitting in a chair, or while riding in a car.

As a related potential benefit, a system and method of a preferred embodiment may alleviate dependence on long-life batteries or active chemical-based power sources with an implant. The increased patient compliance can drive more reliable and regular charging, which may open up medical device design opportunities to use wireless charging in place of the an active or wired power source with the implant.

As another potential benefit, a system and method of a preferred embodiment may alter the design considerations of an external electrical coupling device away from mobility and wearability. An external electrical coupling device 110 that is integrated with a bed or a chair can have less size and weight restrictions than a mobile and/or worn device, and may additionally have less power restrictions. For example, a common wall outlet may be used to power an external electrical coupling device 110. As a result, the external electrical coupling device can be designed with greater functionality. Substantially more computational resources can be used in the system and method, which may be used for enhanced connectivity, computation, monitoring, and/or active stimulation. Through integrating with existing, normal fixtures in a patient's life, the use of an electrical coupling device may be found to be more comfortable.

As another potential benefit, a system and method of a preferred embodiment may provide opportunities for modifying the electrical stimulation of a patient based on patient activities and/or state. Multiple external electrical coupling devices 110 or an external electrical coupling device integrated with multiple fixtures can be used to provide electrical coupling during different use cases and body positions. For example, a patient may be stimulated differently during different stages of sleep or different when sitting or lying down.

As another potential benefit, a system and method of a preferred embodiment may enable remote patient monitoring. A remote monitoring platform can enable usage data and implant information to be accessed remotely by a doctor, a hospital, a manufacturer, researchers, insurance companies, family member or patient, and/or other suitable parties.

2. System

As shown in FIG. 1, a system for use with an electrical implant device with increased patient compliance of a preferred embodiment can include at least one external electrical coupling device 110 integrated into a fixture 120 and an electrical implant 130. In a first preferred variation, the external electrical coupling device is integrated into a bedding fixture. When the patient sleeps or rests in the bed, electrical stimulation can be performed using an implant. In a second preferred variation, the external electrical coupling device 110 is integrated into a chair fixture so that electrical stimulation can be performed using an implant during prolonged periods of sitting. For example, a truck driver may attach the external electrical coupling device 110 to a car seat and receive stimulation while driving. In another preferred variation, the external electrical coupling device may be removably integrated from a fixture so as to be selectively integrated with different fixtures.

2.1 External Electrical Coupling Device

The external electrical coupling device 110 of a preferred embodiment functions as a non-implantable charging and/or communication system that wirelessly powers and communicates with at least one implant. The external electrical coupling device 110 can interact with the implant when the implant is within a zone of energy coupling (i.e., a transmission zone) with the external electrical coupling device 110. The external electrical coupling device 110 preferably includes at least one external energy coupler 112. The external electrical coupling device 110 additionally includes supplementary electrical and computational components used in driving energy coupling, communicating with the implant, storing/processing received data, and/or performing any suitable task of the external electrical coupling device 110 including but not limited to data processing, data storage, communication control, user interface control, and/or other aspects of device functionality.

The external energy coupler 112 of a preferred embodiment functions to facilitate the energy transmission with the implant 130. The external energy coupler 112 is preferably the element used to generate and/or receive wirelessly transmitted signals to an implant. The implant 130 preferably includes one or more complementary implant energy couplers 132. The external energy couplers 112 as well as the implant energy couplers can similarly be designed for inductive or magnetic coupling; electrical radiative coupling, ultrasound, infrared (IR) coupling; and/or other forms of wireless power transmission. The type of external energy coupler 112 is dependent on the medium of wireless power transmission, and any suitable type of antenna, transducer, or power transmission/receiver mechanism may be used. The external energy coupler 112 could be an antenna coil for inductive or magnetic coupling. The external energy coupler 112 could alternatively be an RF antenna (such as a dipole antenna) for electrical radiative coupling, an ultrasonic transducer for ultrasound coupling, and/or an IR emitter for IR coupling.

The energy coupling preferably wirelessly powers an electrical component of the implant 130. In one variation, the implant 130 uses a capacitor to store the energy. The implant 130 can utilize that power for any suitable functionality such as converting to a DC signal for electrical stimulation, electrical sensing, or other suitable uses. In a spinal fusion implant and/or an orthopedic electrical stimulation implant, the energy coupling preferably provides sufficient energy to introduce osteoinduction or osteolyis in the fusion space by electrical stimulation delivered through implant 130.

In some implementations, the external energy coupler 112 is driven with a stimulation signal that directly drives electrical stimulation of the implant 130. In directly driven stimulation the electrical stimulation signals imparted to the body by the implant 130 are based on the energy coupling signal transmitted to the implant 130 by the external energy coupler 112. The stimulation signal may be augmented or adjusted to accommodate various scenarios. In one variation, the stimulation signal may be modified according to stimulation history. Stimulation history may include frequency of stimulation, duration, time since last stimulation, or other suitable analysis of stimulation history. For example, the stimulation signal may be set to compensate when usage is less frequent than expected or prescribed. In another example, the stimulation signal may be attenuated or ceased when stimulation duration is above a maximum threshold within a time window. In another variation, the stimulation signal may be modified according to relative orientation of electrical coupling device 110 and the implant 130. This may be used when the fixture allows a variety of positions suitable for energy coupling. For example, the stimulation signal may be modified based on the sleeping orientation of the patient. The change in the stimulation signal because of orientation change may be performed for a medical reason such as electrical stimulation should use a particular pattern when a patient sleeps on his or her side compared to sleeping on his or her back. The change in the stimulation signal because of an orientation change may alternatively be performed for enhance energy coupling. For example, the sleeping orientation may alter the properties of energy coupling and/or which implant energy coupler 132 is targeted.

The electrical coupling device 110 preferably includes a power source 114 and coupler circuitry 116 with coupler control circuitry and/or coupler communication circuitry.

The power source 114 functions to power the external energy coupler 112. The power source preferably connects to a standard power outlet such as an AC wall outlet, a USB port, a cigarette lighter socket, and/or any suitable power outlet. The power source 114 may additionally or alternatively have a power storage system such as a battery or power generator such as a solar panel. In addition to powering complementary electrical components, the power source 114 is preferably used in driving the external energy coupler 112. In various implementations, the power source 114 may provide DC power to an oscillator circuit, which is effective in transmitting some of this power to the implant 130 by using some of it to generate narrowband AC oscillations within a transmitter coil (acting as an external energy coupler 112) which can generate oscillating electrical signal over an receiver coil (acting as the implant energy coupler 132) through inductive coupling. In other implementations, the power source may be used to generate narrowband AC signals over an RF antenna (e.g., a dipole antenna), an ultrasonic transducer, an IR emitter or another transmitter suitable for wireless energy and/or data transfer. The transmitted power signal preferably couples to a corresponding receiver on or conductively coupled to an implant energy coupler 132 of the implant 130.

The coupler control circuitry 116 may be effective for converting electric power from the power source 114 to a modality that can be transmitted wirelessly to an implantable component (e.g. using Induction, electrical radiative coupling, IR, ultrasound etc.), and may also be effective for managing communications between the various components.

The coupler control circuitry could be effective for generating the wireless power/communication signal that drives the external energy coupler 112 to form an electromagnetic field, acoustic field, or other suitable forms of radiative signal. The coupler control circuitry can create digital signals for turning oscillations in the antenna coil on and off and may be used by the transmitter communication circuitry to transmit a communication.

The coupler communication circuitry may allow the electrical coupling device 110 to communicate with the implant 130. The coupler communication circuitry can be used in communicating with the implant, but can additionally decode or interpret signals received from the implant. The coupler communication circuitry or another communication system may also communicate with user interface component(s), secondary computing devices (e.g., a smart phone, computer, or remote server) and/or other non-implantable components. Preferably, the external energy coupler 112 can be used for wireless power transmission and communication. In alternative implementations, the energy coupler 112 is used for power transmission and communication is executed over a second, alternative communication channel. The energy coupler 112 can be used to provide power to drive a communication module of the implant 130.

In one exemplary implementation, the coupler circuitry may comprise a class-E transmitter circuit generating an oscillating electric current within a transmitter coil that induces a potential over a tuned receiver coil located within the implant 130 through inductive or other wireless coupling.

As described above, in some external electrical coupling device configurations, the exact relative position and orientation of the patient and the external electrical coupling device 110 may not be full restrained. For example, a patient may sleep on their side, back, leaning up on pillows, or any suitable sleeping position. More specifically, the energy coupling between external energy coupler 112 and an implant energy coupler 132 may experience various relative orientations and changes of orientation. The system can preferably accommodate such positioning variations through design of the implant energy coupler(s) 112. In some cases, positioning flexibility may be achieved through an adaptive design of the external electrical coupling device 110 (e.g., use of multiple external energy couplers 112), the adaptive design of the implant 130 (e.g., use of multiple external energy couplers 132), and in other situations through mutual adaptive designs of the implant and external electrical coupling device 110.

Figure 2A:
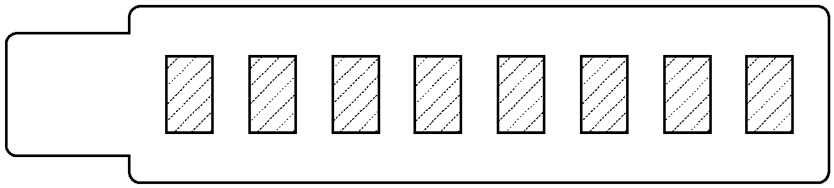
FIGS. 2A, 2B, and 2C are schematic representations of variations of an external electrical coupling device with extended energy coupling coverage.
Figure 2B:
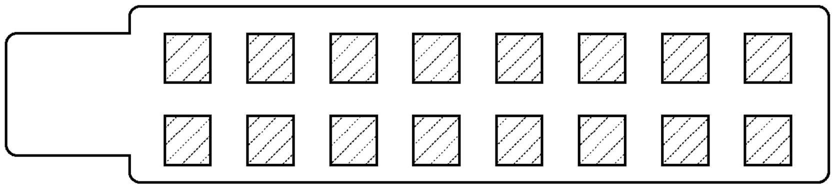
Figure 3:
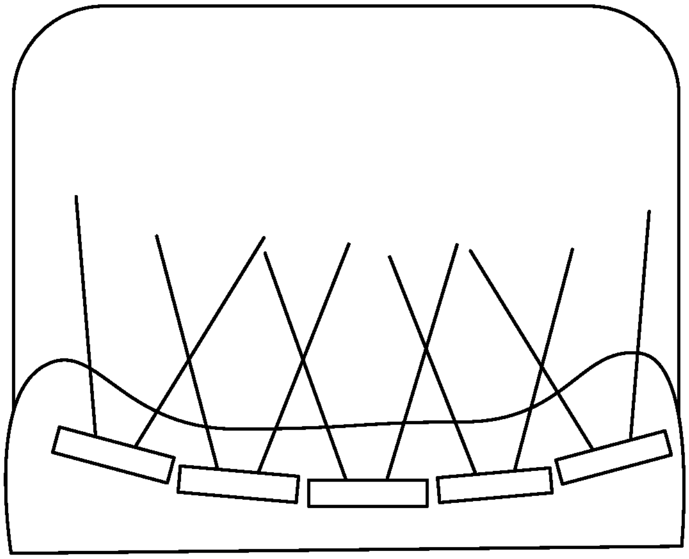
FIG. 3 is a schematic representation of external energy couplers in a seating-based external electrical coupling device where the energy couplers are positioned in non parallel directions.

In one adaptive design, the external electrical coupling device 110 may include a set of energy couplers arranged in an array. An array of electrical energy couplers 113 functions to enable a set of distinct locations and/or orientations for energy coupling. The array of electrical energy couplers can expand the spatial area or volume in which an implant may be positioned. The array of electrical energy couplers 113 can additionally or alternatively expand the compatible orientations of the implant. An array of energy couplers can be a one dimensional array as shown in FIG. 2A. An array of energy couplers can alternatively be a two dimensional array as shown in FIG. 2B. For example, in a radiative coupling system, multiple RF antennas can be positioned at various points across a two-dimensional area of the external electrical coupling device 110. In one variation, each of the external energy couplers 112 is directed in parallel directions. In another variation, at least a first subset and second subset of the energy couplers 112 may be directed in non-parallel directions as shown in FIG. 3. In another variation, the external energy couplers 112 may be tuned (either dynamically or statically). In other words, at least a first subset and second subset of the external energy couplers 112 may be tuned differently.

Figure 4A:
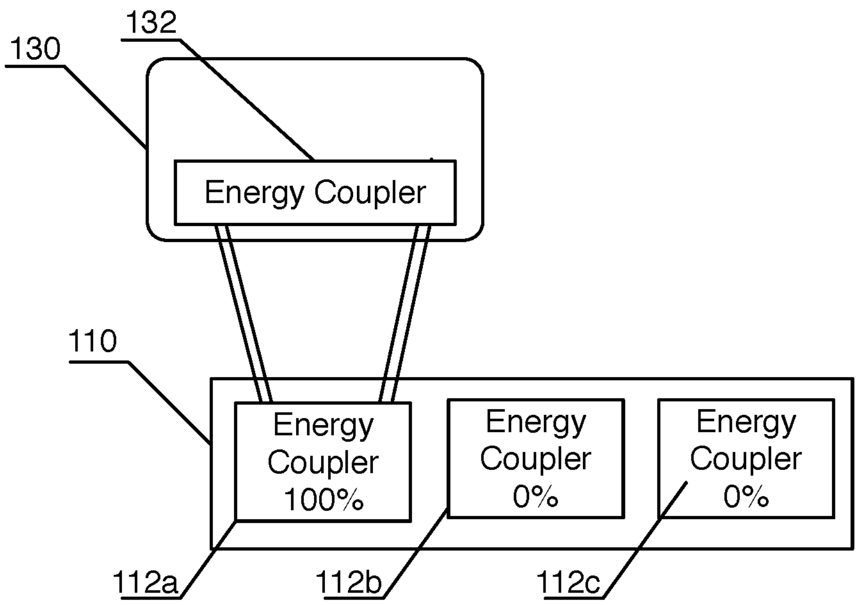
FIGS. 4A-4C are schematic representations of applying a calibration operating mode.
Figure 4B:
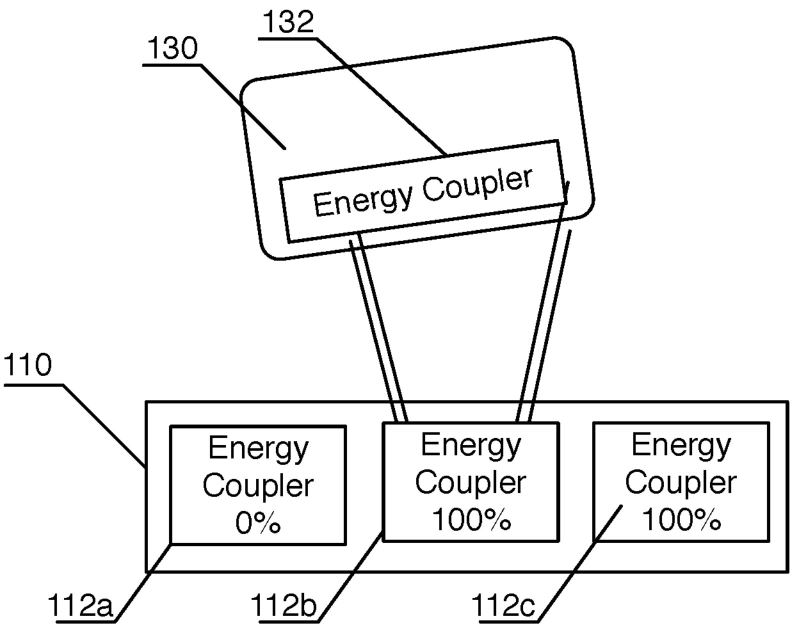
Figure 4C:
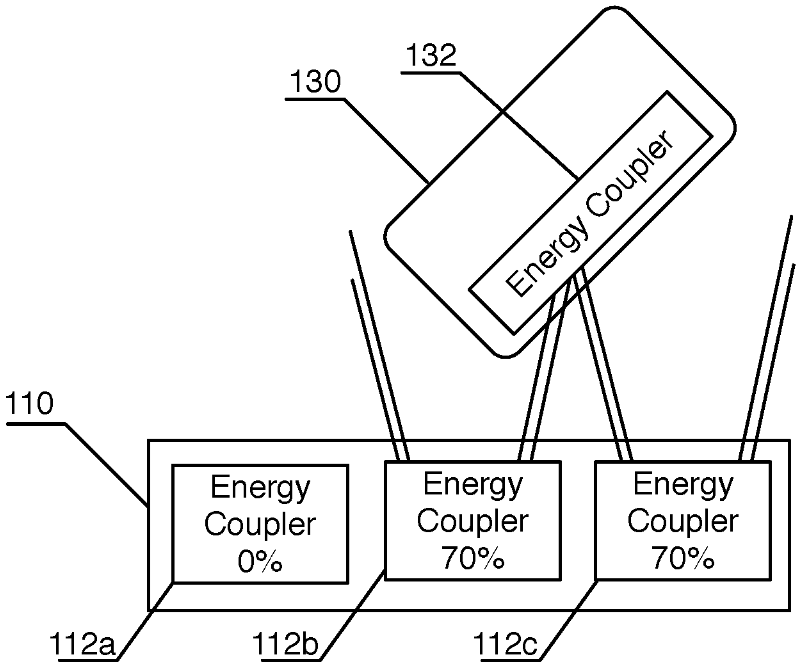

The external energy couplers 112 can be selectively engaged and individually controlled. In one variation, a single external energy coupler 112 of the array 113 may be operated at a given time. Alternatively, multiple external energy couplers 112 can be operated simultaneously. The external electrical coupling device 110 can have a calibration operating mode, wherein transmission energy coupling is cycled across at least a portion of the external energy couplers 112. The implant energy couplers 132 will preferably experience energy coupling to varying degrees. The results can be communicated back to the electrical coupling device 110. The comparison of energy coupling strength may be used to determine a preferred energy coupling mode. The system can dynamically detect and select one or more preferred external energy coupler 112 and use that to interact with the implant 130 during sustained energy coupling. The tuning and/or the control signals of the external energy couplers 112 can additionally be adjusted according to calibration. In a first exemplary scenario shown in FIG. 4A, a first energy coupler 112*a* is used in transmitting power. In a second exemplary scenario shown in FIG. 4B, a second energy coupler 112*b* is used in transmitting power. In a third exemplary scenario shown in FIG. 4C, two external energy couplers 112*b* and 112*c* may be used at seventy percent signal magnitude because of the position and angle of the implant energy coupler. In one implementation, the calibration operating mode is engaged upon the electrical coupling device 110 being activated for use. For example, when a patient first sits down next to a seat fixture, the operating mode is calibrated and that calibration mode is used until the patient sits up. The calibration operating mode may alternatively be periodically or dynamically engaged to adjust how the array of electrical energy couplers 113 is used. For example, the operating mode may be calibrated repeatedly over the course of a night as a patient sleeps on a bed fixture. The external electrical coupling device 110 may additionally or alternatively use beam forming to direct transmissions.

The calibration operating mode may additionally or alternatively be used to sense and detect the relative orientation of the implant and thereby the orientation of the patient. Such a sensing variation of the calibration operating mode (i.e., an orientation sensing mode) is preferably used to determine an orientation at a particular point in time. One sensing approach is substantially similar to the calibration operating mode, the electrical coupling device 110 cycles through multiple external energy couplers 112 of an array 113. The implant energy coupler(s) 132 will preferably experience energy coupling to varying degrees. The results can be communicated back to the electrical coupling device 110. The comparison of energy coupling strength may be used to determine an orientation of the implant. In an alternative approach, orientation sensing can be achieved with a single external energy coupler 112 and preferably multiple implant energy couplers 132. An orientation is preferably determined from the signal strength experienced on the multiple energy couplers 132.

Figure 2C:
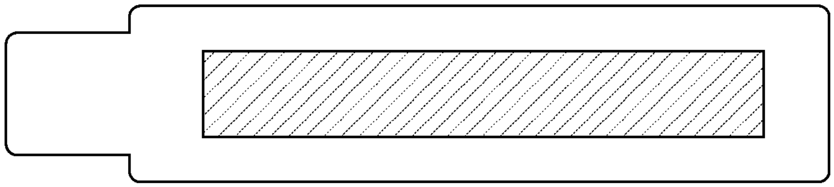

In an alternative implementation, an external energy coupler 112 can be a wide area external energy coupler with a wide coverage area as shown in FIG. 2C. In an inductive coupling system, a single inductance coil may be used, but an array of inductance coils can similarly be used.

Figure 5:
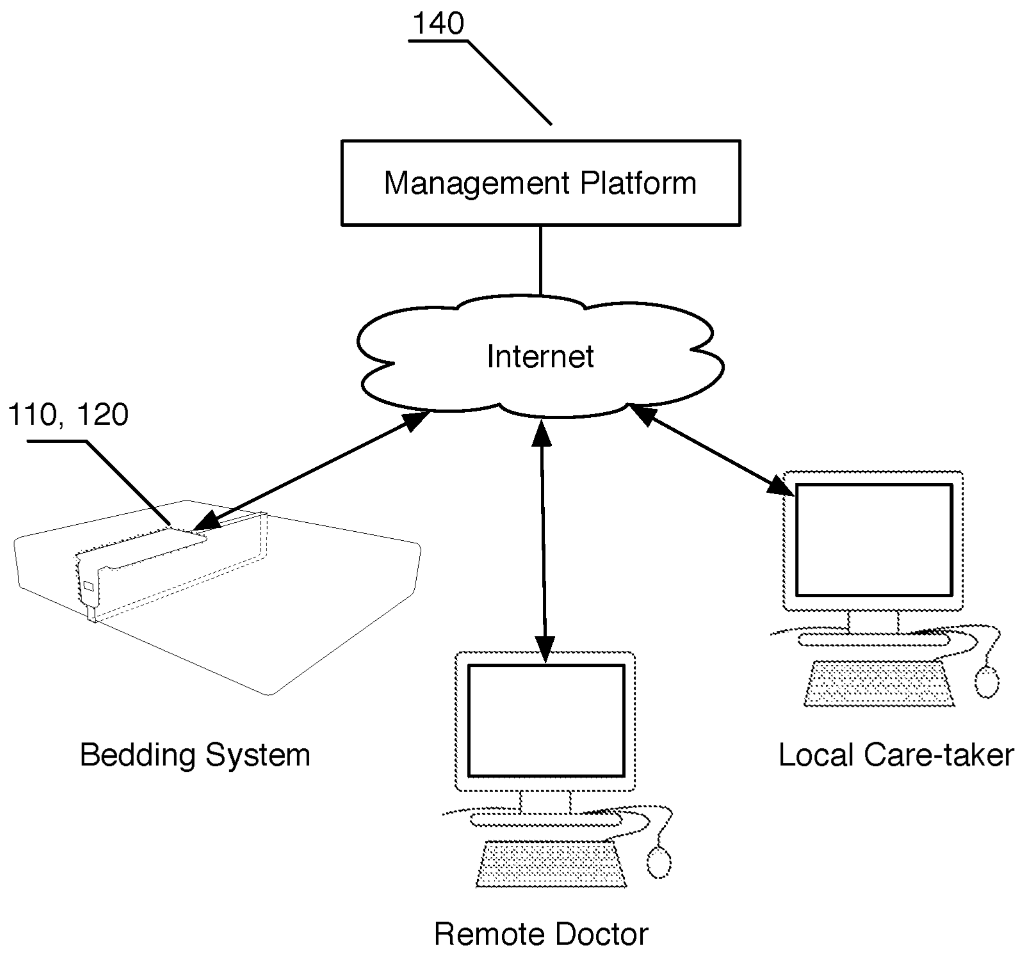
FIG. 5 is a schematic representation of a system including a management platform.

The supplementary components of the external electrical coupling device 110 may include a network module that functions to provide a data connection to other systems. The network module is preferably used to connect to a management platform 140 as shown in FIG. 5. A management platform 140 could be a cloud hosted platform that is in communication with the electrical coupling device 110. The network module can be used to transmit data obtained from the implant (or lack thereof) to a remote destination such as a doctor system, a cloud system, manufacturer system, insurance system, and/or any suitable computing system. The network module can provide a data connection over dial up, Wi-Fi, Bluetooth, carrier networks, and/or any suitable type of data connection. In one alternative a physical data storage solution can enable data to be stored on some device (such as a USB stick) and physically delivered to a doctor. The network module may additionally or alternatively be used to facilitate remote control of the external electrical coupling device and/or the implant 130. For example, a doctor could remotely change the implant 130 settings.

The network module may include communication capabilities for management, remote control, or monitoring by a patient or an administrator such as a doctor, hospital staff, a device manufacturer and the like. The network module may be used to connect with the management platform 140 and/or a control application or device. For example, a potential user may interact with the system through a user interface software application running on a computer, tablet, or smartphone with Wi-Fi or Bluetooth capability. Settings of the electrical coupling device 110 (current amplitude, choice of channels, stimulation frequency if AC is used, frequency of impedance measurements etc.) may be adjusted based on feedback from implant, monitored usage of the system, feedback from the patient, or other information.

The external electrical coupling device 110 can additionally include an activation mechanism that functions to automatically activate the external electrical coupling device 110 when the patient is present. In a first variation, the external electrical coupling device 110 can include an operating mode that periodically checks for presence of an implant 130 similar to the calibration operating mode. If the implant is present then energy coupling can be achieved and a communication signal can be received from the implant 130. In a second variation, a body presence sensor can be used. A mechanical switch, pressure sensitive pad, temperature sensor, optical switch or other suitable sensor can be used to detect patient presence. In another variation, the presence sensor and energy coupling inspection can be used in combination. In some implementations, the activation mechanism may only be utilized under particular conditions. For example, the external electrical coupling device 110 may only probe for the presence of an implant 130 during certain times at night. The activation mechanism could additionally include a user activation mechanism such as a button or a switch that can be used for explicit user control.

The external electrical coupling device 110 can additionally include user interface elements. An user input element could be used to activate the device. User input elements could similarly be used to change operating mode, to request information, or perform any suitable task. An user output element such as a display, an audio speaker, indicator lights, or other element can be used to convey information to the user. In one implementation, a graphical indicator could represent the energy status of the implant. In this implementation, the patient preferably uses the external electrical coupling device 110 frequently enough and for long enough to keep the energy status within a certain threshold.

2.2 Fixture

The fixture 120 functions as the element used to promote alignment and/or suitable proximity of the electrical coupling device 110 and implant 130 such that electrical coupling can be achieved. The fixture 120 is preferably a structure that envelops the electrical coupling device 110, wherein the electrical coupling device 110 is an internal component of the fixture 120. The fixture 120 could alternatively hold or position the electrical coupling device 110 in any suitable manner. The fixture 120 is preferably configured and/or designed for periodic patient proximity. The fixture 120 is preferably part of a regularly encountered object of the patient such that during various parts of the day, over the course of a week, or during any suitable time period a patient will be in close enough proximity to benefit from energy coupling between the electrical coupling device 110 and the implant 130.

The fixture 120 is preferably a static fixture such as a bedding fixture or a sitting fixture. A static fixture is preferably integrated with (e.g., attached to, embedded in, etc.) a piece of furnishing used for sitting, lying down, or any suitable mode of rest. A static fixture 120 is preferably integrated common pieces of furniture or elements encountered during daily life such as a bed or chair. In alternative embodiments, the fixture could be the piece of furniture such as the bed or chair configured to be usable with the electrical coupling device 110. The fixture 120 could alternatively be a worn fixture such as a cervical collar, a lumbar corset, a leg brace, or other suitable type of worn harness. In a spinal fusion implant fixture, the fixture 120 preferably promotes positioning of the electrical coupling device 110 along the spine. Alternative types of fixtures may be used for implants that would benefit from alternative positioning of the electrical coupling device 110.

Figure 7:
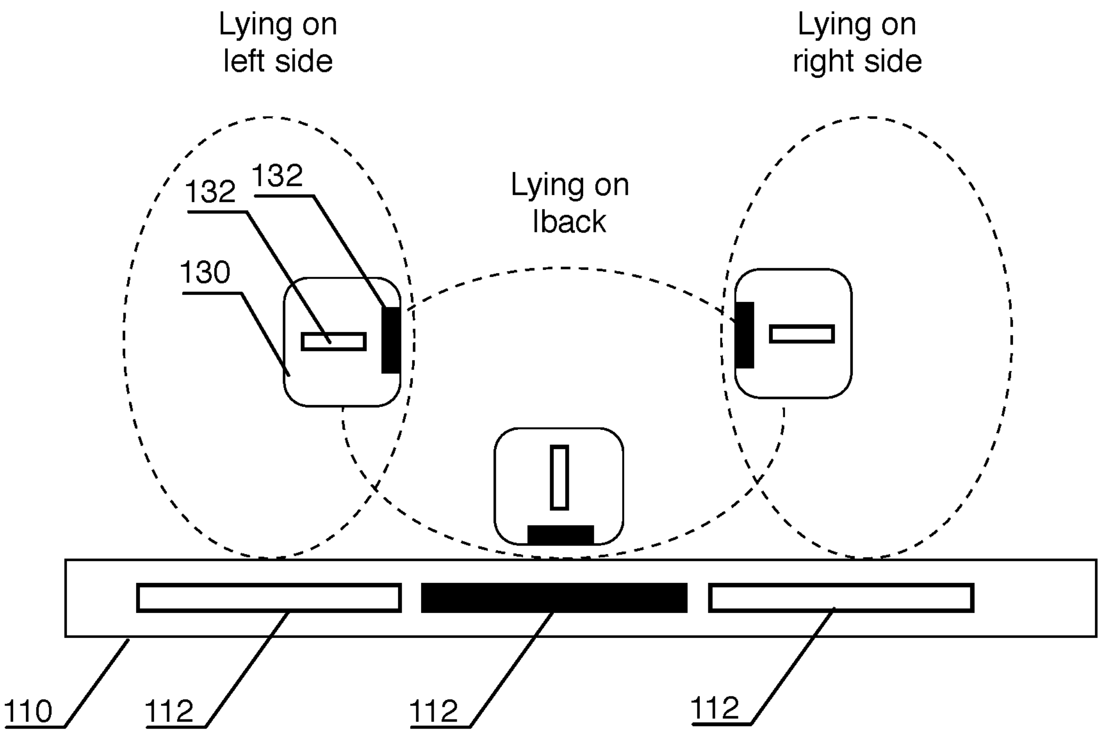
FIG. 7 is a schematic representation of the bedding system used in different sleeping arrangements.

In a first variety, the fixture is a bedding system as shown in FIG. 6A. A bedding system can be integrated with a mattress, a bedding cover, bedding sheet, a bedding pallet, or any suitable system that can be used when sleeping on a bed. Preferably, a bedding fixture 122 is a mat that can be extended across a bed. In one implementation, the bedding fixture 122 can be a foldable mat or pallet as shown in FIG. 6B that can be positioned on a bed as shown in FIG. 6C. The bedding fixture 122 is preferably a substantially flat pallet that can rest above the mattress. The bedding fixture 122 can have an area of coverage that can be extended widthwise across the bed. Extended coverage across the width may accommodate various sleeping positions and changing of those positions during the night. There is preferably an array of external energy couplers 123 distributed across the width. There may additionally or alternatively be an array of external energy couplers 123 distributed lengthwise or distributed in any suitable arrangement. Because the displacement to an implant and the energy coupling may differ when sleeping on one's back compared to sleeping on one's side, the array of external energy couplers can be configured accordingly. A first subset of external energy couplers 112 in a central position may be configured for close proximity, a second and third subset of external energy couplers 112 on either side of the first subset may be configured for a great displacement as shown in FIG. 7. In one variation, different mediums of energy coupling may be used at different points on the array of external energy couplers 113 and for different implant energy couplers 132, which may function to utilize preferred energy coupling mediums depending on the expected positioning scenario. Some mediums of energy coupling may have better performance for greater displacement and being used with greater amounts of intermediary body tissue (i.e., from a patient's side). Some mediums of energy coupling may have better performance for shorter displacement and being used with less intermediary body tissue (i.e., from a patient's back).

In another variation, the implant may include multiple implant energy couplers 132 at different, non-parallel orientations (e.g., aligned to orthogonal planes). A first implant energy coupler 132 may be designed for energy coupling from an external energy coupler 112 at a first displacement that is preferably directed at the back of the patient. The first implant energy coupler 132 may be an antenna coil that is substantially aligned parallel with the coronal plane when the implant is implanted. A second implant energy coupler 132 may be designed for energy coupling from a second external energy coupler 112 at a second displacement that would be directed predominantly to the side of a patient. The second implant energy coupler 132 may be an antenna coil that is substantially aligned parallel with the sagittal plane when the implant is implanted. In a spinal fusion implant, the first displacement (i.e., approximately the distance from the surface of the back to the spine) will be smaller than the second displacement (i.e., approximately the distance from the side of the body to the spine).

If the implant is in the neck or head region, a pillow variation of the bedding fixture 122 may be used. A pillow variation may be used on the top surface of the pillow. Alternatively, a pillow system fixture could be a functional pillow with an integrated electrical coupling device 110. The integrated electrical coupling device 110 is preferably positioned substantially near one surface of the pillow.

Figure 8:
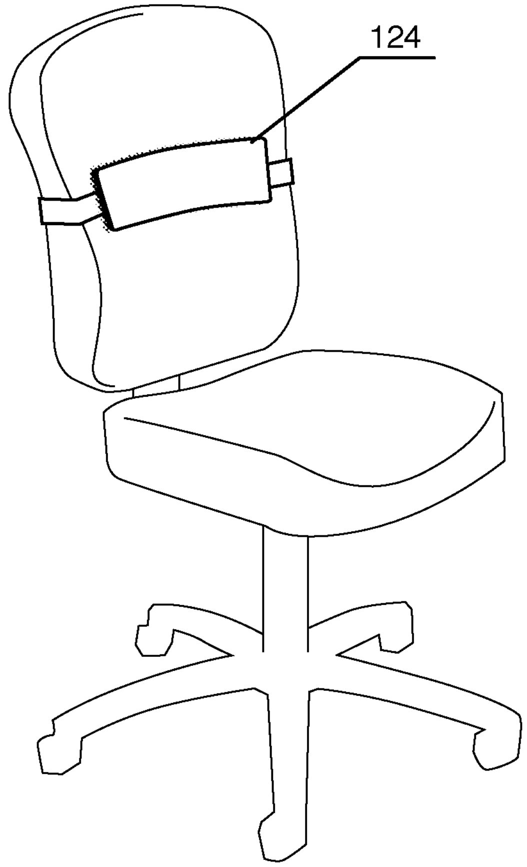
FIG. 8 is a schematic representation of a seating system.

In a second variety, the fixture is a sitting system as shown in FIG. 8. Preferably, a seating fixture 124 is a cover, a seating attachment, a pillow, or any suitable element that can be attached to a piece of furniture used in a sitting position. The seating fixture 124 may include straps or other elements to secure the seating fixture 124 to the back of a seat. In some variations, the seating fixture 124 may be used on the seat portion or on a leg rest. In an alternative implementation of the seating fixture 124, the external electrical coupling device 110 can be directly integrated in a chair-like fixture such as an office chair, a car seat, a couch, a recliner, a wheel chair, or any suitable sitting fixture.

In a sitting fixture 124 variation, the electrical coupling device 110 may accommodate side to side and rotational changes as a patient shifts sitting positions. An array of electrical coupling devices 113 can be, used like in the bedding system 122, where the array is distributed across the width of the seating area. However, a sitting system variation may not need to accommodate for a patient leaning on their side against the fixture 120. Alternatively or additionally, the array may be distributed along the length of the back to accommodate different vertical alignments, which may result from varying degrees of patient slouching.

Figure 9:
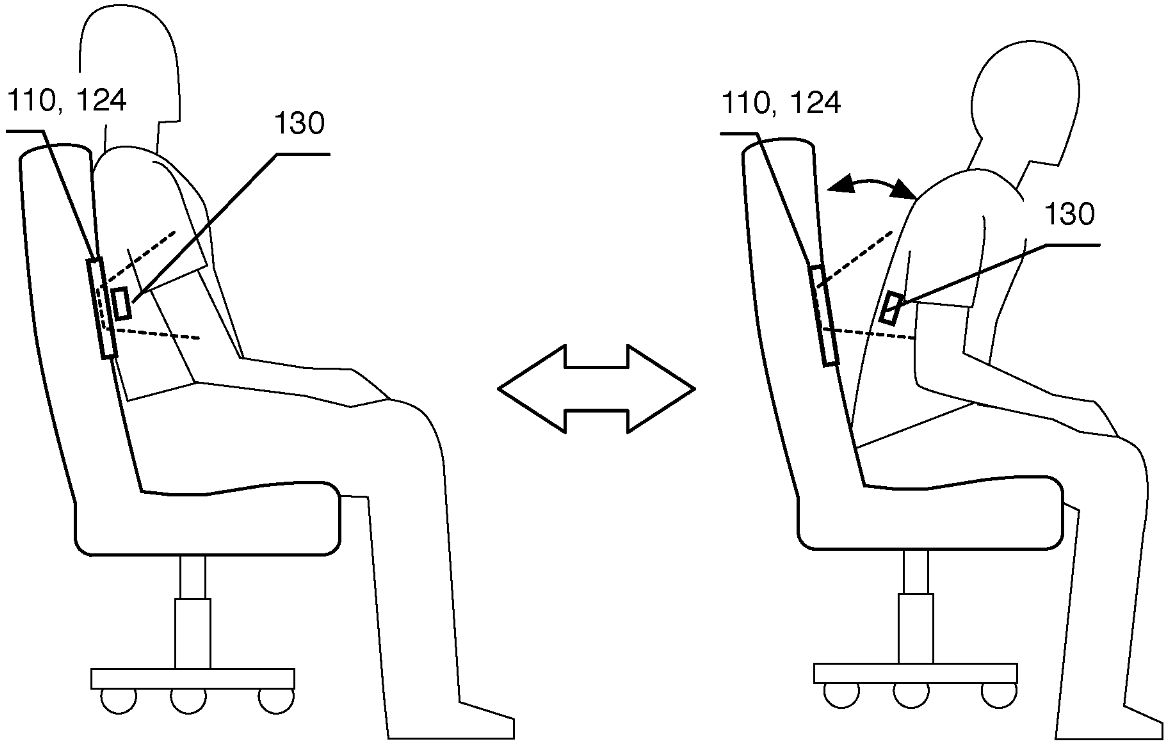
FIG. 9 is a schematic representation of a seating system working with changing sitting positions.

In particular, a sitting fixture 124 variation may accommodate for changes in relative position in the forward-backward direction. For example, when used in a car seat, the patient may shift between leaning back on the fixture and sitting up with the patient's back slightly displaced from the fixture as shown in FIG. 9. When used in a sitting system variation, the electrical coupling device 110 is preferably configured to use a calibration operating mode to adjust energy coupling to account for changes in displacement.

Figure 10:
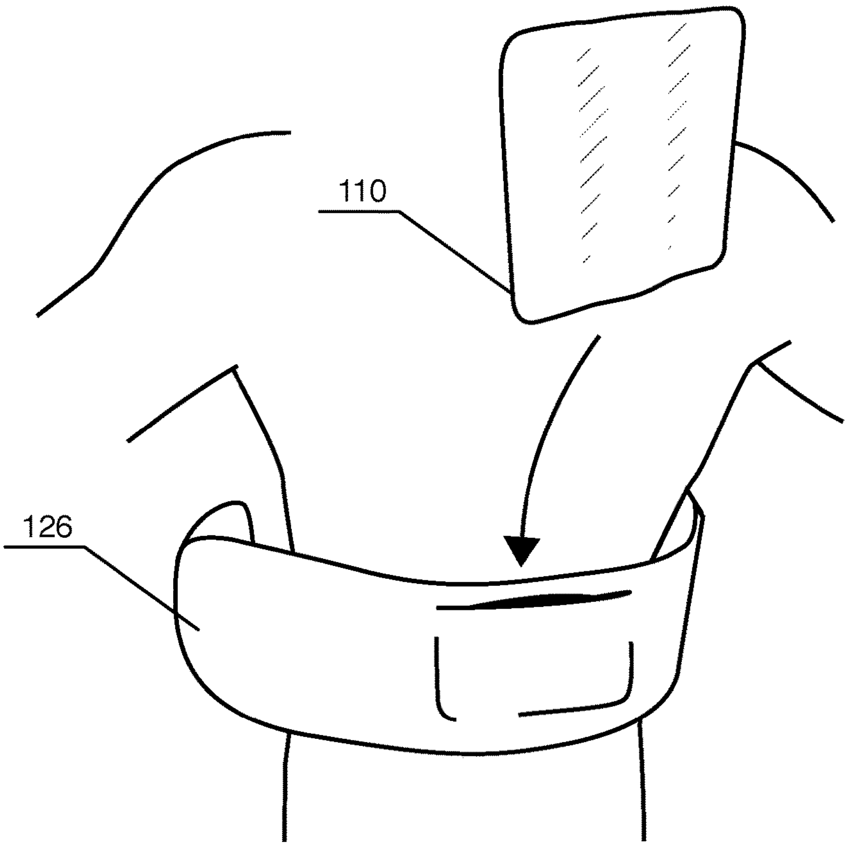
FIG. 10 is a schematic representation of a worn fixture with a removable electrical coupling device.
Figure 11:
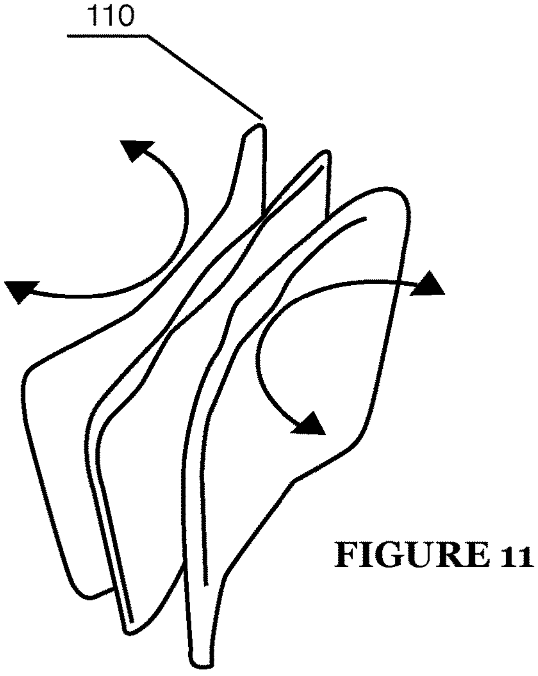
FIG. 11 is a schematic representation of a flexible electrical coupling device.

Another variation of the fixture 120 could be a worn fixture 126 such as a cervical collar, a lumbar corset, a leg brace, a belt, a jacket, pants, a hat, or another or other suitable type of worn harness. The electrical coupling device 110 is preferably removably integrated with a worn fixture 126 as shown in FIG. 10. A worn fixture 126 may include a pocket or sleeve in which the electrical coupling device 110 can be inserted. With a worn fixture the electrical coupling device 110 may be made to be at least partially flexible to conform better to the body as shown in FIG. 11. Alternatively, the electrical coupling device 110 may be substantially permanently integrated. A worn fixture 126 may be similar to those commonly worn by patients following surgery—cervical collars and corsets are already worn by a significant proportion of all patients having undergone spinal fusion surgery. An electrical coupling device 110 can preferably be positioned along or near surfaces of the worn fixture 126 located in close proximity to the implant. A worn fixture may additionally be attached to a patient and restrained so that there will be minimal changes in relative orientation and positioning of the electrical coupling device 110 and the implant 130.

The fixture 120 and/or optionally the external electrical coupling device 110 can include structural features to promote proper alignment and usage. For example, a bedding pallet fixture may include raised inclines on the outer edges to keep a patient within a zone of energy coupling. A sitting-based fixture may include lumbar or neck support structural elements, which promote positioning of the sitting system in the appropriate area of the back. The external electrical coupling device 110 may be designed according to the fixture limitations. In some variations, the external electrical coupling device 110 can be made of flexible and/or stretchable material such as a polymer substrate so as to more comfortably integrate with a fixture.

The external electrical coupling device 110 may additionally be adaptable to be transitioned between different fixture types. For example, an external electrical coupling device 110 may be used with a bedding fixture 122, a seating fixture 124, and/or a worn fixture 126. In another variation, the system can include a variety of external electrical coupling devices 110 integrated into different fixtures 120. Stimulation could be delivered during different activities and timing across the day when a set of external electrical coupling devices 110 is used in different scenarios. For example, the system may include both a bed external electrical coupling device 110 during the night and a sitting external electrical coupling device 110 during the day. Preferably, the implant is interoperable across the set of different external electrical coupling devices 110. Control, communication, and data can be synchronized across the set of external electrical coupling devices 110 to promote enhanced interoperability between different external electrical coupling devices 110. In one variation, the energy coupling in using different fixtures can be synchronized with a remote management platform 140. Alternatively, the implant may maintain state and energy coupling history so that each fixture could independently determine if and how it should interact with the implant 130.

Figure 17:
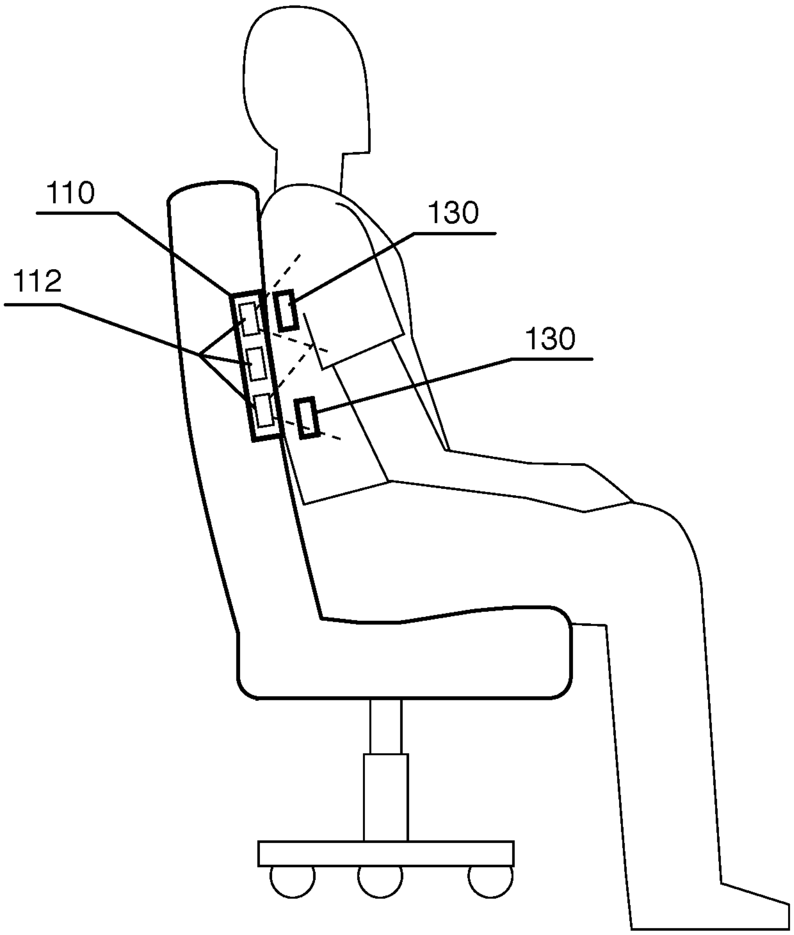
FIG. 17 is a schematic representation of the system used with multiple implants.

In one alternative embodiment, the system may be usable with a plurality of electrical implants. When used for multiple electrical implants 130, the electrical coupling device 110 is configured to cooperatively establish energy coupling with a multiple electrical medical device implants within a transmission zone as shown in FIG. 17. Managing energy coupling with multiple implants may function to allow a single electrical coupling device 110 to be used by a patient with multiple electrical implants 130. Energy coupling may be established from a single external energy coupler 112. Energy coupling may alternatively utilize distinct energy couplers, which could be used simultaneously or at different times.

2.3 Implant

An electrical implant 130 of a preferred embodiment is used within the body to offer some medical functionality. The electrical implant 130 is preferably surgically implanted subcutaneously. In a preferred embodiment, the electrical implant 130 is lacks a wired power connection and is a passive implantable component. A passive implantable component is characterized by not having a battery or active and independent energy supply. A passive implantable component will preferably be dependent on a wirelessly transferred energy supply for sustained use. A short term power storage mechanism such as a capacitor may be used for on device power storage.

Figure 12:
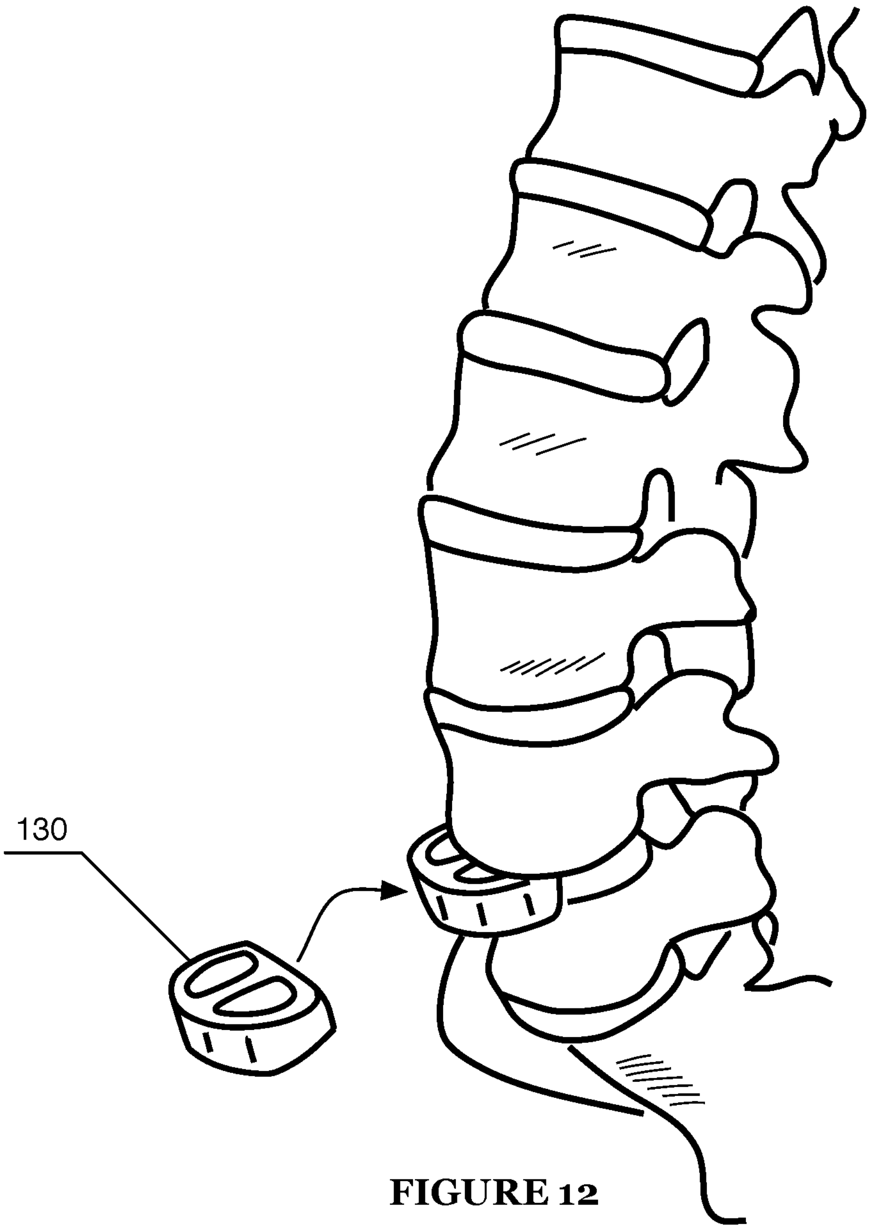
FIG. 12 is a schematic representation of a spinal implant inserted into the spine.

An electrical implant 130 preferably includes at least one component that uses electrical power in operating. A wide variety of medical devices may be used with the system. An electrical implant 130 may use the electrical power for electrical stimulation, medical sensing, communication, and/or other electrically driven functionality. An electrical stimulation implant is preferably used to deliver electrical stimulation to one or more parts of the body. An electrical stimulation spinal fusion implant as shown in FIG. 12 and/or other orthopedic stimulation implants may use the electrical stimulation to promote or control bone growth. Electrical stimulation could also be used to monitor bone growth. The implant may also be an nervous tissue stimulation monitoring implant used to elicit or record electrophysiological activity in central or peripheral nervous tissue. Herein, an electrical orthopedic implant and more specifically an electrical stimulation spinal fusion implant are used as exemplary embodiments, but one knowledgeable and skilled in the art could appreciate how the system could be applied to other types of implants.

Figure 13:
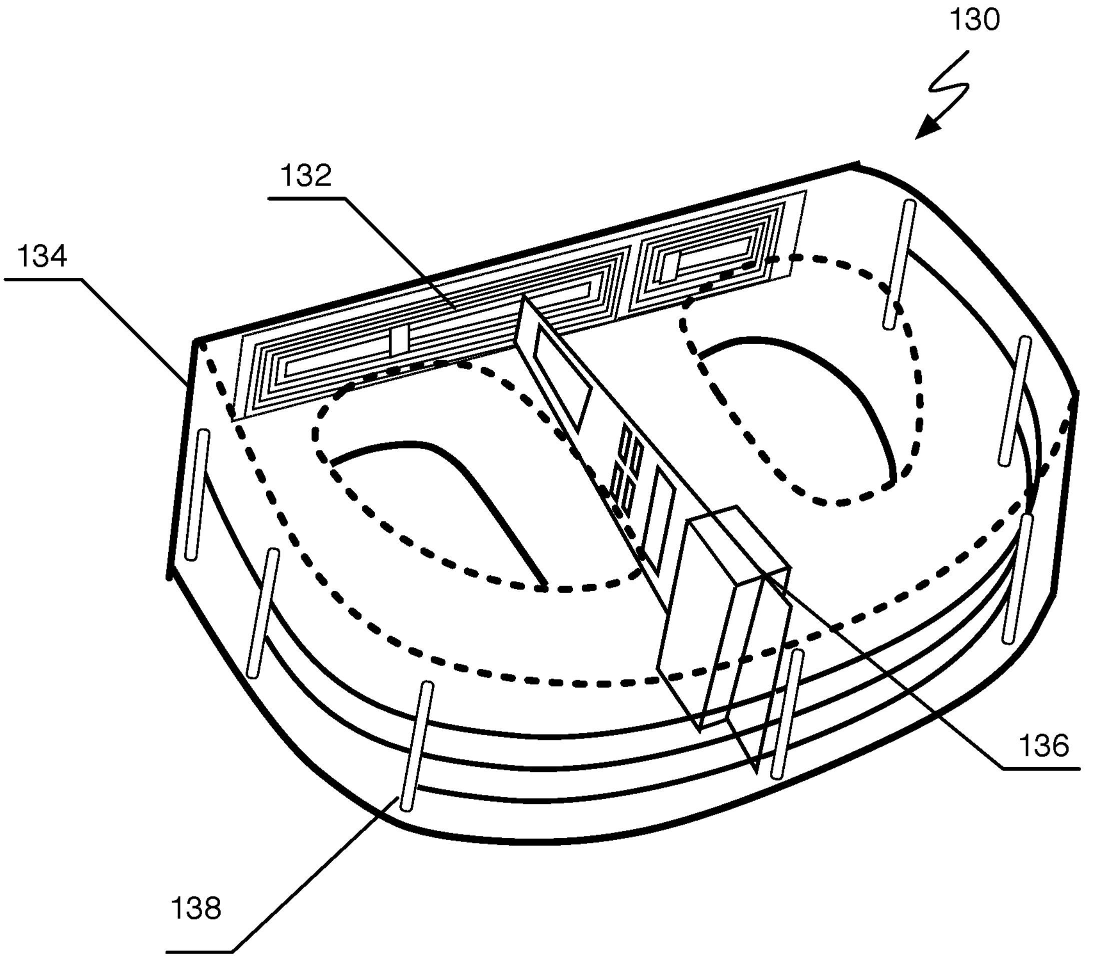
FIG. 13 is a schematic representation of an electrical implant.

The implant 130 may include at least one implant energy coupler 132, an interbody implant body 134, and control circuitry 136 as shown in FIG. 13. An implant 130 may additionally include a set of electrodes 138 in an electrical stimulation variation and/or sensing elements for an electrical sensing variation. Communication may be achievable through the implant energy coupler 132 but communication may alternatively be achieved over a distinct channel or medium using a communication module. The energy to accomplish electrical stimulation, sensing or monitoring, and/or communication between the implant 130 and the external electrical coupling device 110 is preferably wirelessly transmitted through energy coupling. The implant 130 is preferably powered by wirelessly transmitted energy received by at least one implant energy coupler 112. The control circuitry and other supplementary components can manage receiving power from and transmitting data to the external electrical coupling device 110.

Figure 14:
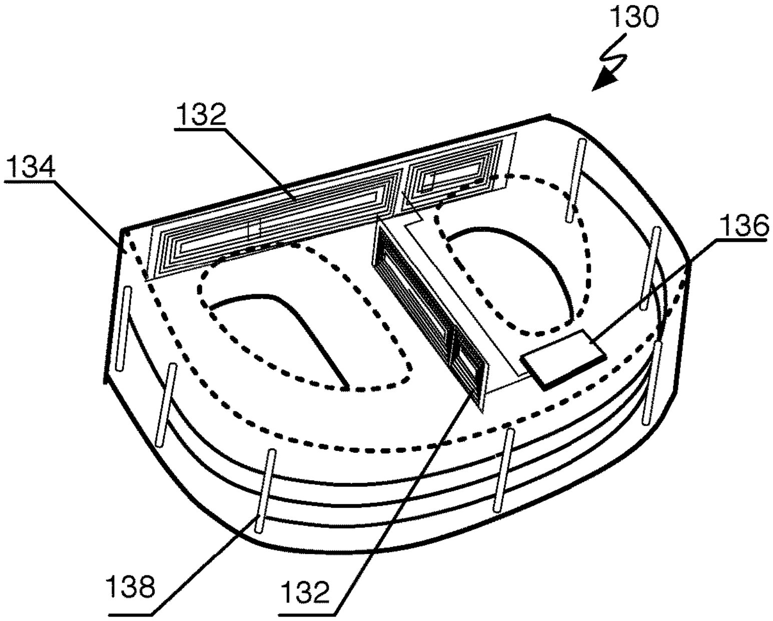
FIGS. 14 and 15 are schematic representations of electrical implants with multiple implant energy couplers.
Figure 15:
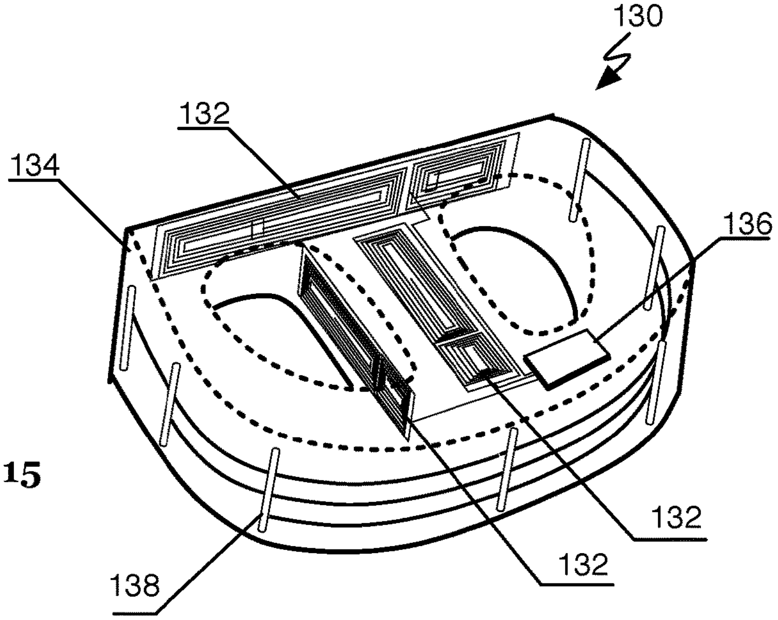

The implant energy coupler 132 of a preferred embodiment receives and/or generates wirelessly transmitted signals. The electrical implant 130 can additionally include a set of implant energy couplers 132 that function to receive and/or generate wirelessly transmitted signals from various directions as shown in FIGS. 14 and 15. An implant energy coupler 132 is preferably used in wireless communication as well as collecting wirelessly transmitted energy for powering various electrical components such as altering the electric fields around implant electrodes. The implant energy coupler 132 is preferably a wireless transmission element that corresponds to an external energy coupler 112 of the external electrical coupling device 110. The type of energy couplers used in the implant 130 and the external electrical coupling device 110 could utilize electrical radiative coupling but can additionally include ultrasound, infrared radiation (IR), and/or any suitable wireless communication/power transmission approach. In various embodiments of an inductively coupled system, the implant energy coupler 132 includes an inductive antenna coil used in inductive coupling for receiving and transmitting electrical signals through an electromagnetic field. Inductive-based energy coupling can operate at low frequencies, which may limit the perturbance of the body, amount of heating effects, allergic reactions, and other potential side effects. A radiative coupled system can include one or more antennas used in receiving RF signals used in communication and powering and also in transmitting communication back to the external electrical coupling device 110.

An implant 130 may not always have the same position and/or orientation relative to an external electrical coupling device 110 because of motion or positioning of the patient. Induction, RF, other forms of wireless energy transfer approaches may be sensitive to position and orientation of the transmitting and receiving parties. The system preferably uses an adaptive design, which functions to promote non-restrictive use of the external electrical coupling device 110 (e.g., a patient can use a bedding system without worrying about keeping his or her back in a particular position or orientation). The external electrical coupling device 110 and/or the implant 130 can alter how energy is transferred to accommodate for change in orientation and position.

In one variation, a plurality of implant energy couplers 132 can be positioned along different non-parallel surfaces so as to expand coverage for receiving power and transmitting data. Preferably, the implant energy couplers 132 and the external energy coupler(s) 112 of the external electrical coupling device 110 have designs to promote operability across a wide range of orientations. In a bedding application, the system can support varying sleeping positions. In a chair application, the system can support shifting motions and angular orientation changes. In some variations, the system can support selective use of a bedding system, chair system, and/or other suitable external electrical coupling device 110 fixtures.

In one implementation, the implant 130 can include two implant energy couplers 132 as shown in FIG. 14. This may be particularly useful in a bedding system variation for targeting back and/or side sleeping. In another implementation, the implant 130 can have three implant energy couplers 132 positioned on the back surface, the top surface, and along a middle side surface as shown in FIG. 15. The back surface, top surface, and the side surface preferably define three orthogonal planes. With the orthogonal plane orientation, energy can be received from various angles. For example, when a patient is lying on her back then the back surface implant energy coupler 132 may be the main receiver of energy. When the patient is lying on her side, the middle side surface may be the main receiver of energy as shown in FIG. 7. In one variation, the received energy can be summed across multiple implant energy couplers. For example, if the patient is lying partially on her side, then the back and side surface implant energy couplers 132 can cooperatively collect the transmitted energy. In another variation, a single implant energy coupler 132 can be selected as the current energy receiver. During energy coupling, the single implant energy coupler 132 with the strongest signal can be used.

Alternative arrangements of implant energy couplers may be used. Depending on the type of fixture 120, implant energy couplers may be positioned and oriented to more closely adapt to the range of transmission profiles encountered for that fixture. For example, the antenna, induction coil, or other suitable implant energy coupler 132 can be positioned along planes at non-orthogonal angles.

The system may be able to detect the position and/or orientation of the electrical coupling device through determining the amount of energy received by energy couplers located on each surface. Such sensing may then be used by onboard circuitry to transmit signals from the implant to the external electrical coupling device 110 to direct how to activate the one or more external energy couplers 112.

The electrical implant 130 can include various circuit modules to address different types of functionality such as power management, communication, and/or implant functionality.

The implant 130 preferably includes power management circuitry. In an exemplary implantation, energy coupling with the electrical coupling device 110 results in an AC signal generated over a receiver coil. A rectifying circuit can convert the AC signal into DC signals. If at any instance, the power of induced DC signals is higher than the sum of the power consumption of the implant 130, the excess power can be stored using capacitor(s). If, at any instance, the sum of the power consumption of the implant 130 exceeds that provided the by power source wirelessly, charge stored within capacitor(s) can be used to partially or fully compensate this discrepancy. In some implementations, charge stored in capacitor(s) may fully power the implant 130 during periods where the electrical coupling device 110 is not actively transmitting power from an external power source.

The electrical implant 130 may additionally include a communication control circuitry. Communication control circuitry can be used to send and/or receive data. Communicated data can relate to state of energy coupling, power state, operating conditions, sensed information, implant directives, and/or other pieces of information. Preferably, communication is transmitted and/or received using the implant energy couplers 132. Alternatively, an alternative communication module may be used. In one variation, communication between the implant 130 and the external electrical coupling device 110 can be cryptographically secured. An electrical implant 130 may be restricted to only being used with a limited set of authenticated electrical coupling devices 110. The electrical implant 130 and/or the electrical coupling device 110 can be configured with the authentication credentials and/or identifiers.

Figure 16:
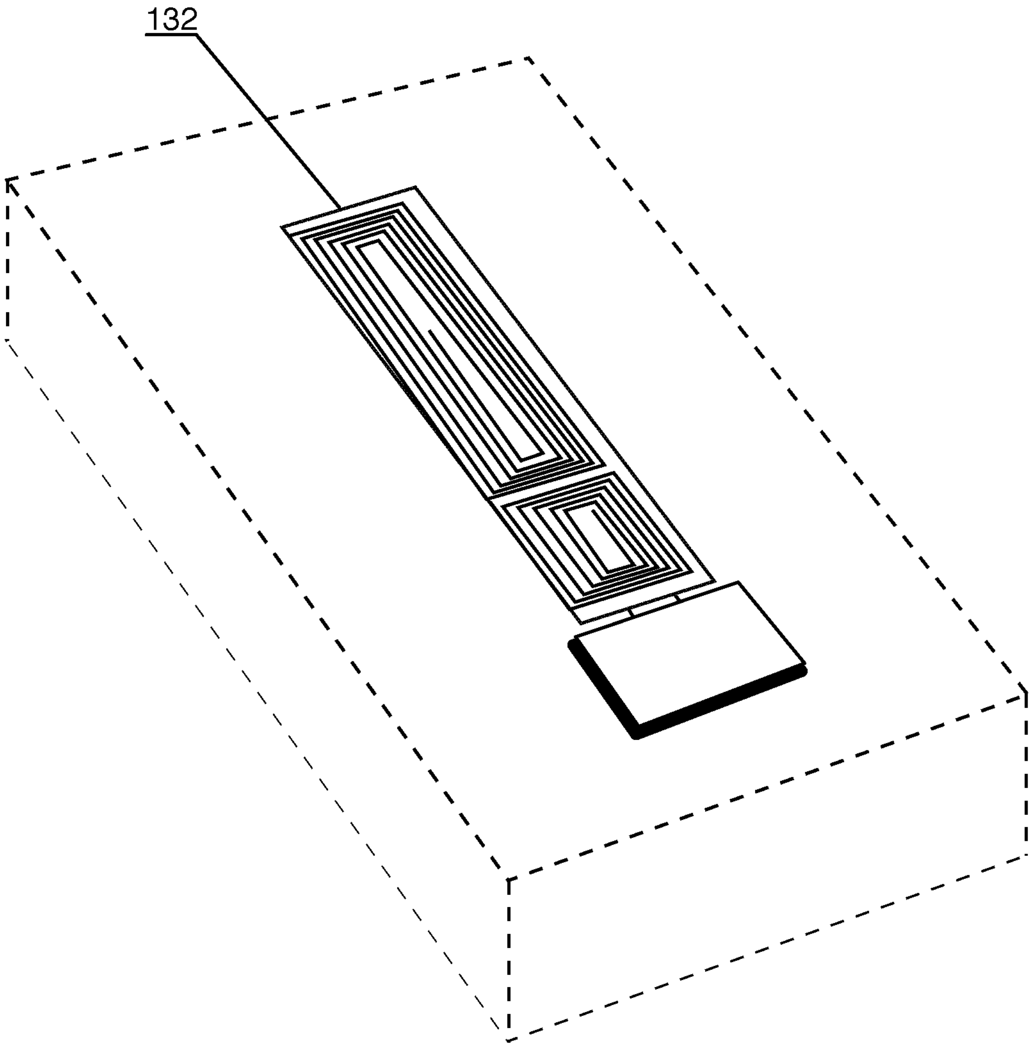
FIG. 16 is a schematic representation of an energy coupler usable with a third party medical device.

The implant body 134 may be a rigid or semi-rigid component that provides substantial structural support as an implantable device. The implant body 134 can be made of a biocompatible material. The implant body 134 may be composed of a polymer such as PEEK, engineered natural or synthetic bone material, titanium, resorbable material and/or any suitable material, and/or combinations thereof. In an electrical stimulation variation, the implant body 134 is nonconductive such that electrical stimulation can be isolated to the electrodes. In some embodiments, the implant body 134 is a spinal implant, which may be a spinal cage. In other embodiments, the implant body 134 may take the form of a thin structure which can be placed on, attached to, envelope an implant structure such as a spinal cage. In some embodiments, the system may provide a power and/or communication system that other outside medical device designers can utilize. In this embodiment, the system may comprise of just an implantable energy coupler and associated components to integrate with an implantable medical device, which functions to enable the system to be used with a variety of implants as shown in FIG. 16. In yet other embodiments the implant body 134 may take the form of a thin film or strip that may be placed within any area within or in the vicinity of the a target body region.

The implant body can have various geometries depending on the type of implant. As mentioned above, one preferred implementation of the system and method is for a spinal fusion implant application. The implant body can be designed with a spinal fusion implant geometry as shown in FIGS. 13-16. A variety of geometries of spinal cages can be used including but not limited to anterior lumbar interbody fusion (ALIF) cages, transforaminal lumbar interbody fusion (TLIF) cages, eXtreme lateral interbody fusion (XLIF) cages, posterior lumbar interbody fusion (PLIF) cages, anterior cervical fusion (ACF) cages, and/or other suitable types of spinal cages.

The implant body 134 may house some or all circuit elements, a PCB, leads, antennas, and other suitable components included as part of the implant. In an electrical stimulation variation, the implant body 134 may additionally include integrated electrode sites distributed across the geometry of the implant body 134 in such a way as to facilitate the generation of osteolytic or osteoinductive regions throughout the fusion space. Stimulating current can be isolated to the surface of the electrode sites, thus allowing the distribution of current density to be controlled by the placement of the electrodes as well as their state during stimulation. In some variations, an insulating layer or element can border the electrodes to provide electrical isolation from a conductive implant body. In various variations, a conductive surface or element of the implant body may be used as an electrode element.

The electrical implant 130 can include set of electrodes 138 in an electrical stimulation variation. Individual or subsets of the electrodes are preferably independently controllable and spatially distributed such that current driven between different subsets of electrodes can be used to generate osteolysis and osteoinduction within one or multiple target bone volumes. Utilizing an adequate number of electrodes distributed strategically throughout the fusion space, synergistic combinations of anodes and cathodes may be used to create regions of osteolysis and osteoinduction in multiple volumes of bone located at multiple locations within the fusion space. This approach may be used to sculpt fusion mass quantity and distribution towards a shape that benefits fusion outcomes by steering both the magnitude and location of increased or decreased fusion mass. To further aid sculpting of the fusion mass, certain implementations of the inventive implant system may also include circuitry to adjust the intensity of delivered stimulation by adjusting the amplitude of current driven between electrodes. Such adjustments may increase or decrease the volume of bone affected by stimulation and/or increase or decrease the effect with which stimulation causes osteoinduction and/or osteolysis within volumes of bone affected by an applied stimulation.

An electrical stimulation orthopedic implant functions as a surgically inserted medical device that may promote bone repair through the passive structure of the implant and/or through actively modulating bone growth by osteoinduction and/or osteolysis. Osteoinduction is the promotion of bone growth, and osteolysis is the promotion of bone reabsorption. Osteoinduction and osteolysis are preferably actively modulated by providing electrical stimulation of various regions in and around the electrical orthopedic implant. The implant may additionally or alternatively electrically monitor bone growth during the healing process and/or perform other suitable electrically driven processes such as stimulation of central and/or peripheral nervous tissue. Bone growth may be monitored by performing impedance measurements between pairs of single or multiple electrodes so that the impedance of the tissue between such pairs can be monitored. Since the impedance of bone is different than other tissue, a change in impedance between a pair may be used to estimate state of the fusion mass between that pair.

3. Method

Figure 18:
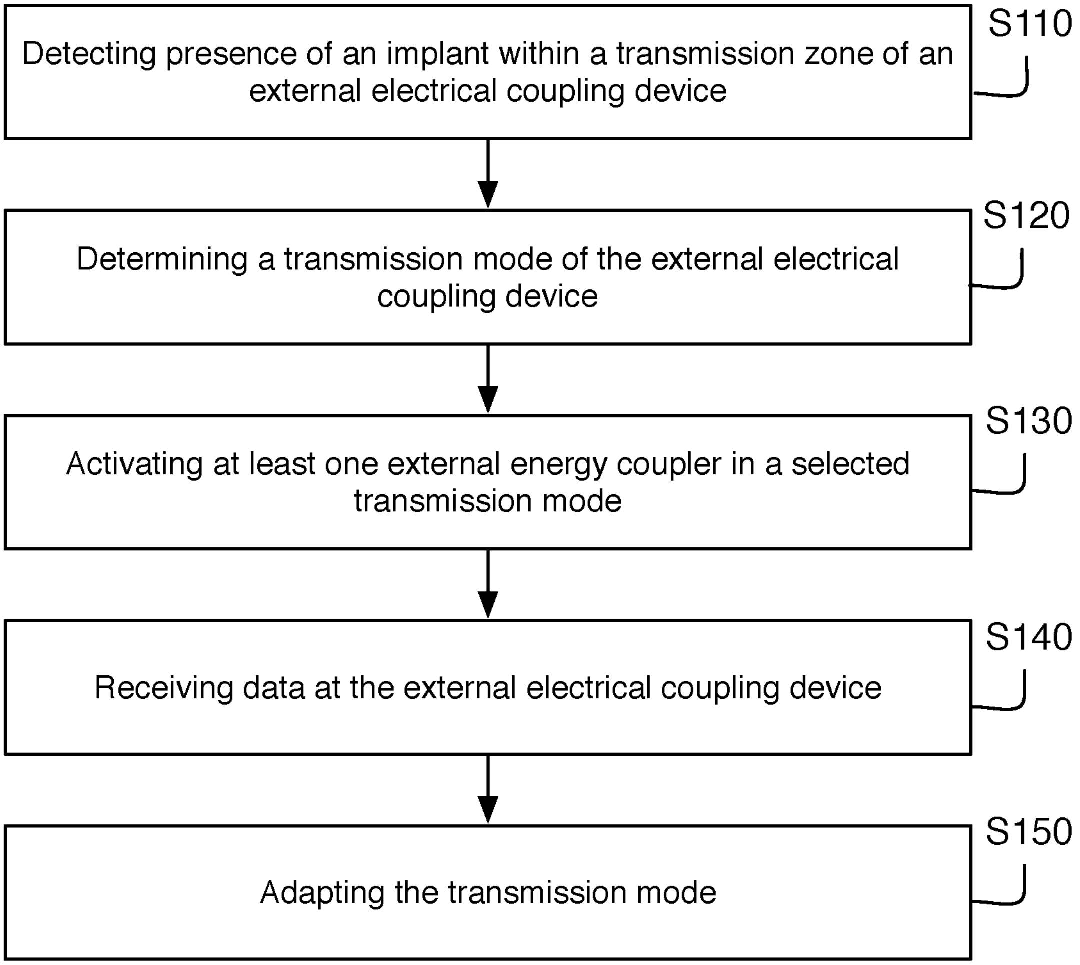
FIG. 18 is a flow diagram of a method of a preferred embodiment.

As shown in FIG. 18, a method for a surgical implant stimulation device used to increased patient compliance of a preferred embodiment can include detecting the presence of an implant within a transmission zone of an external electrical coupling device S110, determining a transmission mode of the external electrical coupling device S120, and activating at least one external energy coupler in a selected transmission mode S130. The method preferably enables the external electrical coupling device and/or the implant to dynamically adapt the mode of energy coupling to provide a wide range of patient positioning. The external electrical coupling device is preferably integrated with a convenient fixture where the external electrical coupling device is not fixed to a localized spot on the body. The patient may move and shift such that the energy coupling for the stimulation signal and for data communication must adapt to achieve adequate signal levels. The method is preferably implemented by a system substantially similar to the system described above, but any suitable system may alternatively be used.

Block S110, which includes detecting presence of an implant within a transmission zone of an external electrical coupling device, functions to determine when stimulation of an electrical implant can be performed. In a first variation, detecting presence of an implant can include the external electrical coupling device periodically polling for an implant signal. An external electrical coupling device periodically transmits a signal, which may result in energy coupling with an implant within the transmission zone. An implant that is compatible with the external stimulation and in the transmission zone will receive the signal from the external electrical coupling device, and can respond. An external electrical coupling device can be temporarily or permanently paired for transmission to a specific implant. An authentication security exchange may be executed prior to an implant accepts use of an external electrical coupling device. For example, an external electrical coupling device may be paired and configured for use with a patient's implant before the external electrical coupling device is sent home with the patient. The implant will be restricted to only accepting communication (e.g., stimulation signals) from an authenticated external electrical coupling device. The transmitted signal may include cryptographic information. The implant can verify the signal, and, if authenticated, can send an acknowledgment to the external electrical coupling device.

In an alternative implementation, an external electrical coupling device may be used with a variety of implants. Detecting presence of an implant additionally includes detecting the implant identity and selecting associated operating modes. For example, in a hospital where, beds or wheelchairs may be shifted between patients, an external electrical coupling device will detect the identity of the implant through a communicated identifier and then apply the proper settings. The way the patient is stimulated can be customized per patient, and the data collected from an implant is associated with that implant identifier.

In an alternative embodiment, detecting presence of an implant may include detecting patient presence from a supplementary presence signal. For example, a mechanical switch may be triggered when a patient rests against the external electrical coupling device. Alternatively, a patient may provide the activation signal through some user interface element. In one variation, the external electrical coupling device can include an inertial measurement unit, which may include a multi-axis accelerometer, gyroscope, or other suitable motion sensor. Disturbances to the external electrical coupling device can wake the device and initiate detection of implants within the energy coupling zone. In another variation, a proximity sensor may be used to determine when to check for an implant. A proximity sensor preferably generates an electrical signal when an object comes within a particular range of the proximity sensor. In one example, a proximity sensor can be used with a seating fixture variation, so that the electrical coupling device will only try to achieve energy coupling when the proximity sensor indicates an object, presumably the patient, is present.

Block S120, which includes determining a transmission mode of the external electrical coupling device, functions to determine how an external energy coupler is used for energy coupling. Determining a transmission mode can include cycling transmission through the array of external energy couplers, detecting a response to the transmissions, and selecting the energy coupler associated with the response that is indicative of the strongest transmission. Depending on the orientation of the patient, one or more of the external energy couplers will transmit a signal that is most strongly received by the implant. A stronger transmission can result in greater wireless power transfer to the implant.

In a similar manner, an implant can determine a receiving operating mode. The implant can include a set of different implant energy couplers, which may be antennas, induction coils, or other receiving/transmitting elements. The implant can extract received energy from multiple implant energy couplers, but may alternatively select the implant energy coupler with the strongest signal for use during stimulation. The implant energy coupler receiving the strongest signal can additionally be used for transmission to the external electrical coupling device. If different implant energy couplers are used for receiving and transmission of power/data, the system may be able to detect the location of the electrical coupling device by determining the amount of energy received by implant energy couplers located on each surface. Communication circuitry may be used to communicate such positioning information back to the external electrical coupling device.

Block S130, which includes activating at least one external energy coupler in a selected transmission mode, functions to wirelessly send an electrical signal to the implant from an external source. The wireless signal can be used in providing power and/or data transfer. The wireless signal is preferably sent from the selected energy coupler of the transmission mode. The selected transmission mode preferably indicates the subset of external energy couplers to use during transmission. The selected transmission mode can additionally specify a transmission signal to use when activating the external energy coupler(s).

At the implant, the implant energy coupler receives the wirelessly transmitted signal through the energy coupling. The resulting electrical signal may be converted from an AC signal to a DC signal using rectifying circuitry. If at any instance, the power of induced DC signals is higher than the sum of the power consumption of all implantable component(s) and any power used to stimulate tissue, the excess power can be stored using power storage components (e.g., capacitors). If, at any instance, the sum of the power consumption of all implantable component(s) and any power used to stimulate tissue exceeds that provided the by power source through wireless coupling, charge stored within power storage components can be used to partially or fully compensate this discrepancy. In some implementations, charge stored in power storage component may fully power the implantable component(s) and/or stimulate tissue in during periods where the transmitter is not actively transmitting power from a power source.

The method can additionally include receiving data at the external electrical coupling device S140, which functions to receive communication from the implant. As described above, the implant preferably uses at least one implant energy coupler in transmitting. The implant may selectively transmit from the implant energy coupler that received the strongest signal since that can indicate that that energy coupler is in the best orientation for wireless power transfer and communication. Alternatively, the implant may transmit communication signal from multiple energy couplers. The transmission may be made simultaneously or repeatedly one at a time. The external electrical coupling device can receive data at the selected energy coupler used in transmitting and/or other energy couplers. The external electrical coupling device may alternatively detect received data across a set of energy couplers.

The method can additionally include adapting the transmission mode S150, which functions to modify how the at least one external energy coupler is activated during transmission. When a patient moves, the previous energy coupler used in transmitting and/or receiving in the external electrical coupling device and the implant can change. The transmission mode is preferably modified to adjust for any orientation or alignment changes between the patient and the external electrical coupling device. In one variation, the transmission mode can be dynamically altered based on strength of the stimulation signal transfer or the strength of the data transfer from the implant. For example, if the data signal from the implant grows weaker or becomes undetectable, then block S120 can be repeated to determine a better way to transmit. In another variation, the external electrical coupling device can detect motion using an IMU or any suitable motion-sensing device. Similarly, block S120 can be repeated to determine a better mode of transmission.

In an electrical stimulation variation, stimulating modes can be changed according to patient state when using the particular external electrical coupling device. These stimulation modes can be dependent on the type of external electrical coupling device. There can be customized stimulation patterns and sequences for when a patient is sleeping, sitting or walking. In another variation, the system could change stimulation based on sleep cycle. The stimulation patterns may be modified over the course of one night to improve recovery. The implant preferably provides stimulation for some amount of time while the patient uses the fixture. However, in some cases, the patient may not receive sufficient amounts of stimulation. The method can include signaling the status of stimulation quantity. In one implementation, the external electrical coupling device can activate a visual signal or make an auditory signal representative of what percentage of daily stimulation was achieved in a given time period. This stimulation quantity can additionally be synchronized across multiple external electrical coupling devices.

The method can additionally include communicating with an external resource. The external stimulating device can send received data from the implant to one or more remote resources. The data from the implant may be synchronized with a device management platform. Doctors and other interested parties can monitor the rehabilitation progress. A doctor could additionally monitor compliance and see if a patient is receiving sufficient stimulation. In one variation, diagnostics routines can be performed on the implant and synchronized with a remote resource. Communication with an external resource can additionally include receiving control inputs. For example, a doctor could alter the stimulation parameters.

The systems and methods of the embodiments can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a user computer or mobile device, wristband, smartphone, or any suitable combination thereof. Other systems and methods of the embodiment can be embodied and/or implemented at least in part as a machine configured to receive a computer-readable medium storing computer-readable instructions. The instructions can be executed by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor but any suitable dedicated hardware device can (alternatively or additionally) execute the instructions.

As a person skilled in the art will recognize from the previous detailed description and from the figures and claims, modifications and changes can be made to the embodiments of the invention without departing from the scope of this invention as defined in the following claims.

We claim:

1. A system for powering a medical device comprising:

an electrical orthopedic implant that is a passive implantable component, wherein the electrical orthopedic implant comprises an implant body and at least a first implant energy coupler positioned on the implant body and a second implant energy coupler positioned on the implant body along a distinct, non-parallel surface from the first implant energy coupler;

a fixture configured for periodic patient proximity;

an external electrical coupling system integrated into the fixture wherein the external electrical coupling system comprises an array of external energy couplers configured to detect presence of the electrical orthopedic implant in a transmission zone of the external electrical coupling device; and wherein the external electrical coupling system is configured to couple to the electrical orthopedic implant through a wireless energy transmission between at least one external energy coupler of the array of external energy couplers and the implant energy coupler when presence of the electrical orthopedic implant is within the transmission zone; and wherein the external electrical coupling system is further configured to be selectively engaged for simultaneous wireless energy transmission from multiple external energy couplers in the array of external energy couplers to at least one of the first or second implant energy couplers.

2. The system of claim 1, wherein the fixture is a bedding fixture.

3. The system of claim 1, wherein the fixture is a seating fixture.

4. The system of claim 1, wherein the fixture is a static fixture integrated with a piece of furnishing; and further comprising a worn fixture, wherein the external electrical coupling system is removably integrated with the static fixture and the worn fixture.

5. The system of claim 1, wherein the external electrical coupling system further comprises a calibration operating mode configured to adjust energy coupling by the external energy coupler system.

6. The system of claim 1, wherein the array of external energy couplers comprises of external energy couplers positioned across a two-dimensional area of the fixture, and wherein the array of external energy couplers comprises a first subset of external energy couplers in a first region with a first configuration and at least a second subset of external energy couplers in a second region with a second configuration.

7. The system of claim 6, wherein the first subset of external energy couplers of the array is in a configuration directed in a first direction and the second subset of external energy couplers of the array is in a configuration directed in a second direction, wherein the first and second directions are non-parallel.

8. The system of claim 6, wherein a subset of external energy couplers of the array of external energy couplers is used during energy coupling.

9. The system of claim 6, wherein the external electrical coupling system is configured to cycle energy coupling transmission across a subset of external energy couplers and select at least one energy coupler for use during sustained energy coupling.

10. The system of claim 1, wherein the electrical orthopedic implant further comprises a set of electrodes usable in delivering electrical stimulation.

11. The system of claim 10, wherein the electrical orthopedic implant is a spinal fusion cage implant.

12. The system of claim 1, wherein an external energy coupler of the array is an inductive coil; wherein the implant energy coupler is an inductive coil; and wherein the energy coupling is inductive coupling.

13. The system of claim 1, wherein the medium of energy coupling is radiative coupling selected from radio frequency electric radiative coupling, ultrasound, and infrared coupling.

14. The system of claim 1, further comprising a remote management platform with network communication access to the electrical coupling device.

15. The system of claim 1, further comprising at least a second electrical orthopedic implant; and wherein the external electrical coupling system is configured to cooperatively establish energy coupling with a plurality of electrical orthopedic implants within the transmission zone.

16. A system for use with an orthopedic implant device comprising:

at least a first implant energy coupler positioned on an implant body of the orthopedic implant device and a second implant energy coupler positioned on the implant body of the orthopedic implant device, the second implant energy coupler being positioned along a non-parallel surface from the first implant energy coupler;

a fixture configured for periodic patient proximity;

an external electrical coupling device integrated into the fixture wherein the external electrical coupling device comprises an array of external energy couplers and is configured to:

detect presence of at least one of the first implant energy coupler and the second implant energy coupler when within a transmission zone of the external electrical coupling device, determine a transmission mode of the external electrical coupling device, in a first transmission mode, couple to at least one of the first implant energy coupler and the second implant energy coupler through a wireless energy transmission between an external energy coupler of the array and at least one of the first implant energy coupler and second implantable energy coupler, in a second transmission mode, couple at least one of the first implant energy coupler and the second implant energy coupler through simultaneous wireless energy transmissions between two external energy couplers of the array and at least one of the first implant energy coupler and second implantable energy coupler, and receive data at the external electrical coupling device transmitted by at least one of the first implant energy coupler and the second implant energy coupler.

17. The system of claim 16, wherein the fixture is a bedding fixture.

18. The system of claim 16, wherein the fixture is a seating fixture.

19. The system of claim 1, wherein the electrical orthopedic implant is a passive implantable component that has no battery.

20. The system of claim 1, wherein the electrical orthopedic implant further comprises a set of electrodes integrated into the implant body, and wherein the wireless energy transmission powers electrical stimulation through the set of electrodes.

21. The system of claim 6, wherein the first subset of external energy couplers of the array is tuned differently from the second subset of external energy couplers.

* * * * *